(12) United States Patent
Giovangrandi

(10) Patent No.: US 10,881,310 B2
(45) Date of Patent: Jan. 5, 2021

(54) MOTION ARTIFACT MITIGATION METHODS AND DEVICES FOR PULSE PHOTOPLETHYSMOGRAPHY

(71) Applicant: The Board of Trustees of the Leland Stanford Junior University, Palo Alto, CA (US)

(72) Inventor: Laurent B. Giovangrandi, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 554 days.

(21) Appl. No.: 13/974,758

(22) Filed: Aug. 23, 2013

(65) Prior Publication Data

US 2014/0058217 A1 Feb. 27, 2014

Related U.S. Application Data

(60) Provisional application No. 61/693,270, filed on Aug. 25, 2012.

(51) Int. Cl.
*A61B 5/0295* (2006.01)
*A61B 5/00* (2006.01)
*A61B 5/1455* (2006.01)

(52) U.S. Cl.
CPC ........ *A61B 5/0295* (2013.01); *A61B 5/14552* (2013.01); *A61B 5/721* (2013.01)

(58) Field of Classification Search
CPC . A61B 5/0295; A61B 5/1455; A61B 5/14551; A61B 5/14552; A61B 5/02416;

(Continued)

(56) References Cited

U.S. PATENT DOCUMENTS 5,040,539 A 8/1991 Schmitt et al.
5,111,817 A 5/1992 Clark et al.
(Continued)

FOREIGN PATENT DOCUMENTS

WO WO 2011/029029 3/2011
WO WO 2013/052574 4/2013

OTHER PUBLICATIONS

H. Tandri et al. "Reversible Cardiac Conduction Block and Defibrillation with High-Frequency Electric Field." Sci Transl Med 3(102), Sep. 28, 2011, 16 pgs.

(Continued)

*Primary Examiner* — Niketa I Patel
*Assistant Examiner* — Nathan A Baldwin
(74) *Attorney, Agent, or Firm* — Crawford Maunu PLLC

(57) ABSTRACT

Aspects of the present disclosure are directed toward devices, apparatus, and methods for interfacing a PPG apparatus with the skin surface of a patient and sensing artifacts due to surface motion attributable to contact-based surface motion at or near where the apparatus in contact with the skin surface of the patient. The devices, apparatus, and methods include circuitry that contacts the skin surface of the patient, illuminates tissue at the surface, and senses a pulse photoplethysmography (PPG) signal of the patient in response thereto. Further, the circuitry senses artifacts due to surface motion, and responds to the sensed PPG signal by processing the sensed PPG signal relative to the sensed artifacts to produce a version of the sensed PPG signal that is indicative local blood volume and composition of the patient, and filtered to suppress noise therein due to the contact-based surface motion.

13 Claims, 8 Drawing Sheets

(58) Field of Classification Search
CPC . A61B 5/02427; A61B 5/02433; A61B 5/024; A61B 5/0261
See application file for complete search history.

(56) References Cited

U.S. PATENT DOCUMENTS

| | | |
|---|---|---|
| 5,450,846 A | 9/1995 | Goldreyer |
| 5,672,875 A | 9/1997 | Block et al. |
| 5,792,998 A | 8/1998 | Gardner, Jr. et al. |
| 5,859,652 A | 1/1999 | Silverbrook |
| 5,909,227 A | 6/1999 | Silverbrook |
| 6,010,836 A | 1/2000 | Eichorst et al. |
| 6,064,065 A | 5/2000 | Block et al. |
| 6,139,819 A | 10/2000 | Unger et al. |
| 6,169,914 B1 | 1/2001 | Hovland et al. |
| 6,231,834 B1 | 5/2001 | Unger et al. |
| 6,261,236 B1 | 7/2001 | Grimblatov |
| 6,380,294 B1 | 4/2002 | Babinec et al. |
| 6,408,198 B1 | 6/2002 | Hanna et al. |
| 6,420,709 B1 | 7/2002 | Block et al. |
| 6,431,173 B1 | 8/2002 | Hoffmann |
| 6,491,647 B1 | 12/2002 | Bridger et al. |
| 6,521,211 B1 | 2/2003 | Unger et al. |
| 6,535,754 B2 | 3/2003 | Fishbein et al. |
| 6,549,801 B1 | 4/2003 | Chen et al. |
| 6,586,520 B1 | 7/2003 | Canorro et al. |
| 6,699,199 B2 | 3/2004 | Asada et al. |
| 6,707,257 B2 | 3/2004 | Norris |
| 6,731,967 B1 | 5/2004 | Turcott |
| 6,754,535 B2 | 6/2004 | Noren et al. |
| 6,839,585 B2 | 1/2005 | Lowery et al. |
| 6,905,470 B2 | 6/2005 | Lee et al. |
| 6,997,879 B1 | 2/2006 | Turcott |
| 7,020,507 B2 | 3/2006 | Scharf et al. |
| 7,058,272 B2 | 6/2006 | Bourdelais et al. |
| 7,130,689 B1 | 10/2006 | Turcott |
| 7,194,306 B1 | 3/2007 | Turcott |
| 7,254,425 B2 | 8/2007 | Lowery et al. |
| 7,277,741 B2 | 10/2007 | Debreczeny et al. |
| 7,288,584 B2 | 10/2007 | Highcock et al. |
| 7,300,166 B2 | 11/2007 | Agrawal et al. |
| 7,329,402 B2 | 2/2008 | Unger et al. |
| 7,452,551 B1 | 11/2008 | Unger et al. |
| 7,477,924 B2 | 1/2009 | Chin |
| 7,483,731 B2 | 1/2009 | Hoarau et al. |
| 7,486,979 B2 | 2/2009 | Matlock |
| 7,499,740 B2 | 3/2009 | Nordstrom et al. |
| 7,507,579 B2 | 3/2009 | Boccazzi et al. |
| 7,515,949 B2 | 4/2009 | Norris |
| 7,519,413 B1 | 4/2009 | Morris et al. |
| 7,522,948 B2 | 4/2009 | Chin |
| 7,545,903 B2 | 6/2009 | Kohler et al. |
| 7,555,327 B2 | 6/2009 | Matlock |
| 7,574,244 B2 | 8/2009 | Eghbal et al. |
| 7,574,245 B2 | 8/2009 | Arizaga Ballesteros |
| 7,590,439 B2 | 9/2009 | Raridan et al. |
| 7,629,400 B2 | 12/2009 | Hyman |
| 7,641,614 B2 | 1/2010 | Asada et al. |
| 7,647,084 B2 | 1/2010 | Eghbal et al. |
| 7,650,177 B2 | 1/2010 | Hoarau et al. |
| 7,657,294 B2 | 2/2010 | Eghbal et al. |
| 7,657,295 B2 | 2/2010 | Coakley et al. |
| 7,657,296 B2 | 2/2010 | Raridan et al. |
| 7,674,230 B2 | 3/2010 | Reisfeld |
| 7,676,253 B2 | 3/2010 | Raridan, Jr. |
| 7,684,842 B2 | 3/2010 | Ollerdessen |
| 7,684,843 B2 | 3/2010 | Coakley et al. |
| 7,691,067 B2 | 4/2010 | Westbrook et al. |
| 7,693,559 B2 | 4/2010 | Raridan et al. |
| 7,712,673 B2 | 5/2010 | Jones |
| 7,720,516 B2 | 5/2010 | Chin et al. |
| 7,725,146 B2 | 5/2010 | Li et al. |
| 7,725,147 B2 | 5/2010 | Li et al. |
| 7,725,187 B1 | 5/2010 | Nabutovsky et al. |
| 7,727,159 B2 | 6/2010 | Choi et al. |
| 7,728,048 B2 | 6/2010 | Labrec |
| 7,729,736 B2 | 6/2010 | Raridan, Jr. |
| 7,738,155 B2 | 6/2010 | Agrawal |
| 7,738,935 B1 * | 6/2010 | Turcott ............... A61B 5/0261 600/336 |
| 7,738,937 B2 | 6/2010 | Coakley et al. |
| 7,756,580 B1 | 7/2010 | Turcott |
| 7,787,946 B2 | 8/2010 | Stahmann et al. |
| 7,789,311 B2 | 9/2010 | Jones et al. |
| 7,794,406 B2 | 9/2010 | Reisfeld et al. |
| 7,796,403 B2 | 9/2010 | Coakley |
| 7,803,118 B2 | 9/2010 | Reisfeld et al. |
| 7,803,119 B2 | 9/2010 | Reisfeld |
| 7,824,029 B2 | 11/2010 | Jones et al. |
| 7,839,416 B2 | 11/2010 | Ebensberger et al. |
| 7,839,417 B2 | 11/2010 | Ebensberger et al. |
| 7,857,768 B2 | 12/2010 | Starr et al. |
| 7,869,849 B2 | 1/2011 | Ollerdessen et al. |
| 7,869,850 B2 | 1/2011 | Hoarau et al. |
| 7,879,564 B2 | 2/2011 | Brice et al. |
| 7,881,762 B2 | 2/2011 | Kling et al. |
| 7,894,869 B2 | 2/2011 | Hoarau |
| 7,899,510 B2 | 3/2011 | Hoarau |
| 7,904,130 B2 | 3/2011 | Raridan, Jr. |
| 7,907,809 B2 | 3/2011 | Korampally et al. |
| 7,912,672 B2 | 3/2011 | Feichtinger et al. |
| 7,920,919 B1 | 4/2011 | Nabutovsky |
| 7,924,972 B2 | 4/2011 | Koehler et al. |
| 7,929,220 B2 | 4/2011 | Sayag |
| 7,980,596 B2 | 7/2011 | Labrec |
| 7,998,080 B2 | 8/2011 | Ben-Ari et al. |
| 8,034,898 B2 | 10/2011 | Caravan et al. |
| 8,060,171 B2 | 11/2011 | Hoarau et al. |
| 8,073,516 B2 | 12/2011 | Scharf et al. |
| 8,073,518 B2 | 12/2011 | Chin |
| 8,093,062 B2 | 1/2012 | Winger |
| 8,095,192 B2 | 1/2012 | Baker, Jr. |
| 8,140,143 B2 | 3/2012 | Picard et al. |
| 8,145,288 B2 | 3/2012 | Baker, Jr. |
| 8,152,732 B2 | 4/2012 | Lynn et al. |
| 8,157,730 B2 | 4/2012 | LeBoeuf et al. |
| 8,162,841 B2 | 4/2012 | Keel et al. |
| 8,175,670 B2 | 5/2012 | Baker, Jr. et al. |
| 8,175,671 B2 | 5/2012 | Hoarau |
| 8,190,224 B2 | 5/2012 | Hoarau |
| 8,190,225 B2 | 5/2012 | Hoarau |
| 8,195,263 B2 | 6/2012 | Drebreczeny et al. |
| 8,195,264 B2 | 6/2012 | Hoarau |
| 8,204,567 B2 | 6/2012 | Petersen |
| 8,204,786 B2 | 6/2012 | LeBoeuf et al. |
| 2002/0183611 A1 | 12/2002 | Fishbein et al. |
| 2003/0139667 A1 | 7/2003 | Hewko et al. |
| 2003/0166998 A1 | 9/2003 | Lowery et al. |
| 2003/0208239 A1 | 11/2003 | Lu |
| 2003/0212336 A1 | 11/2003 | Lee et al. |
| 2003/0225337 A1 | 12/2003 | Scharf et al. |
| 2004/0030230 A1 | 2/2004 | Norris |
| 2004/0147832 A1 | 7/2004 | Fishbein et al. |
| 2005/0038349 A1 | 2/2005 | Choi et al. |
| 2005/0043608 A1 | 2/2005 | Haj-Yousef |
| 2005/0054939 A1 | 3/2005 | Ben-Ari et al. |
| 2005/0165316 A1 | 7/2005 | Lowery et al. |
| 2005/0192488 A1 | 9/2005 | Bryenton et al. |
| 2005/0203357 A1 | 9/2005 | Debreczeny et al. |
| 2005/0209516 A1 | 9/2005 | Fraden |
| 2005/0243053 A1 * | 11/2005 | Liess ................ G06F 3/0421 345/156 |
| 2006/0047214 A1 | 3/2006 | Fraden |
| 2006/0211930 A1 | 9/2006 | Scharf et al. |
| 2006/0264755 A1 | 11/2006 | Maltz et al. |
| 2007/0004977 A1 | 1/2007 | Norris |
| 2007/0053482 A1 | 3/2007 | Kohler et al. |
| 2007/0055163 A1 | 3/2007 | Asada et al. |
| 2007/0070800 A1 | 3/2007 | Virag et al. |
| 2007/0106137 A1 | 5/2007 | Baker, Jr. et al. |
| 2007/0167844 A1 | 7/2007 | Asada et al. |
| 2007/0213619 A1 | 9/2007 | Linder |
| 2007/0213620 A1 | 9/2007 | Reisfeld |
| 2007/0213621 A1 | 9/2007 | Reisfeld et al. |

(56) References Cited

U.S. PATENT DOCUMENTS

| | | |
|---|---|---|
| 2007/0213622 A1 | 9/2007 | Reisfeld |
| 2007/0213624 A1 | 9/2007 | Reisfeld et al. |
| 2007/0244399 A1 | 10/2007 | Kim et al. |
| 2008/0009690 A1 | 1/2008 | Debreczeny et al. |
| 2008/0081961 A1 | 4/2008 | Westbrook et al. |
| 2008/0132798 A1 | 6/2008 | Hong et al. |
| 2008/0133171 A1 | 6/2008 | Feichtinger et al. |
| 2008/0146892 A1 | 6/2008 | Le Boeuf et al. |
| 2008/0190430 A1 | 8/2008 | Melker et al. |
| 2008/0200787 A1 | 8/2008 | Shapira et al. |
| 2008/0238695 A1* | 10/2008 | Yanai ............... A61B 5/02427 340/576 |
| 2008/0287815 A1 | 11/2008 | Chon et al. |
| 2009/0043179 A1 | 2/2009 | Melker et al. |
| 2009/0054752 A1 | 2/2009 | Jonnalagadda et al. |
| 2009/0105556 A1 | 4/2009 | Fricke et al. |
| 2009/0118598 A1* | 5/2009 | Hoarau ............... A61B 5/14552 600/301 |
| 2009/0203998 A1* | 8/2009 | Klinghult ........... A61B 5/02416 600/443 |
| 2009/0209834 A1 | 8/2009 | Fine |
| 2009/0221888 A1 | 9/2009 | Wijesiriwardana |
| 2009/0227853 A1 | 9/2009 | Wijesiriwardana |
| 2009/0227965 A1 | 9/2009 | Wijesiriwardana |
| 2009/0232379 A1 | 9/2009 | Kohler et al. |
| 2009/0281399 A1 | 11/2009 | Keel et al. |
| 2009/0281435 A1 | 11/2009 | Ahmed et al. |
| 2009/0292193 A1 | 11/2009 | Wijesiriwardana |
| 2009/0326351 A1 | 12/2009 | Addison et al. |
| 2010/0004517 A1 | 1/2010 | Bryenton et al. |
| 2010/0016691 A1 | 1/2010 | Watson et al. |
| 2010/0079279 A1 | 4/2010 | Watson et al. |
| 2010/0094147 A1 | 4/2010 | Inan et al. |
| 2010/0145201 A1 | 6/2010 | Westbrook et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168589 A1 | 7/2010 | Banet et al. |
| 2010/0168596 A1 | 7/2010 | Jaeschke et al. |
| 2010/0192952 A1 | 8/2010 | Melker et al. |
| 2010/0217099 A1 | 8/2010 | LeBoeuf et al. |
| 2010/0217102 A1* | 8/2010 | LeBoeuf ............... A61B 5/00 600/310 |
| 2010/0241186 A1 | 9/2010 | Turcott |
| 2010/0268056 A1 | 10/2010 | Ricard et al. |
| 2010/0312131 A1 | 12/2010 | Naware et al. |
| 2010/0331715 A1 | 12/2010 | Addison et al. |
| 2011/0004072 A1 | 1/2011 | Fletcher et al. |
| 2011/0009754 A1 | 1/2011 | Wenzel et al. |
| 2011/0009755 A1 | 1/2011 | Wenzel et al. |
| 2011/0040345 A1 | 2/2011 | Wenzel et al. |
| 2011/0046498 A1 | 2/2011 | Klap et al. |
| 2011/0054279 A1 | 3/2011 | Reisfeld et al. |
| 2011/0066041 A1 | 3/2011 | Pandia et al. |
| 2011/0066042 A1 | 3/2011 | Pandia et al. |
| 2011/0066381 A1 | 3/2011 | Garudadri et al. |
| 2011/0071366 A1 | 3/2011 | McKenna |
| 2011/0082355 A1 | 4/2011 | Eisen et al. |
| 2011/0098112 A1 | 4/2011 | LeBoeuf et al. |
| 2011/0098583 A1 | 4/2011 | Pandia et al. |
| 2011/0106627 A1 | 5/2011 | LeBoeuf et al. |
| 2011/0112442 A1 | 5/2011 | Meger et al. |
| 2011/0125208 A1 | 5/2011 | Karst et al. |
| 2011/0144460 A1 | 6/2011 | Oh et al. |
| 2011/0144461 A1 | 6/2011 | Oh et al. |
| 2011/0172504 A1 | 7/2011 | Wegerich |
| 2011/0184297 A1 | 7/2011 | Vitali et al. |
| 2011/0224518 A1 | 9/2011 | Tindi et al. |
| 2011/0245633 A1 | 10/2011 | Goldberg et al. |
| 2011/0251503 A1 | 10/2011 | Ben-Ari et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257553 A1 | 10/2011 | Banet et al. |
| 2011/0257554 A1 | 10/2011 | Banet et al. |
| 2011/0257555 A1 | 10/2011 | Banet et al. |
| 2011/0301436 A1 | 12/2011 | Teixeira |
| 2012/0022336 A1 | 1/2012 | Teixeira |
| 2012/0022350 A1 | 1/2012 | Teixeira |
| 2012/0022384 A1 | 1/2012 | Teixeira |
| 2012/0022844 A1 | 1/2012 | Teixeira |
| 2012/0065527 A1 | 3/2012 | Gill et al. |
| 2012/0065528 A1 | 3/2012 | Gill et al. |
| 2012/0078066 A1 | 3/2012 | Ahmed et al. |
| 2012/0078119 A1 | 3/2012 | Ahmed et al. |
| 2012/0078120 A1 | 3/2012 | Ahmed et al. |
| 2012/0078130 A1 | 3/2012 | Ahmed et al. |
| 2012/0078321 A1 | 3/2012 | Blomqvist et al. |
| 2012/0108928 A1 | 5/2012 | Tverskoy |
| 2013/0303922 A1* | 11/2013 | Buchheim .......... A61B 5/02416 600/479 |

OTHER PUBLICATIONS

M. Z. Poh et al. "Non-contact, automated cardiac pulse measurements using video imaging and blind source separation." Optics Express 18(10), May 2010, pp. 10762-10774.

* cited by examiner

MOTION ARTIFACT MITIGATION METHODS AND DEVICES FOR PULSE PHOTOPLETHYSMOGRAPHY

FIELD OF THE INVENTION

This invention relates to methods and devices for physiologic monitoring, pulse oximetry or heart rate monitoring. In particular, the invention relates to photoplethysmography.

BACKGROUND

Photoplethysmography (PPG) is a technique used in the determination of heart rate and blood oxygen saturation (e.g., pulse oximetry). PPG is often measured using optical detection of a pulsatile change in blood volume in highly-innervated tissues (e.g., fingers, ear lobes). Measuring PPG by optical detection can include illuminating the tissue with typically one wavelength (or two for pulse oximetry) using a light emitter (e.g., a light emitting diode (LED), and measuring the transmission (transmission PPG) or scattering (reflectance PPG) with a photodetector (e.g., photodiode, phototransistor).

PPG and pulse oximetry measurements are susceptible to motion artifacts. Minute movements of the light emitter and/or sensor with respect to the tissue will introduce artifacts which can render extraction of the underlying signal difficult, and can corrupt the calculation of the oxygen saturation value.

SUMMARY

Various aspects of the present disclosure are directed toward such above-discussed and other apparatuses and methods for interfacing with a patient.

Consistent with certain exemplary embodiments, the disclosure describes apparatuses and methods that utilize two circuits operative for contacting highly-innervated tissue (e.g., the skin surface of a person or patient) with one of the circuits illuminating tissue at the surface by sending light toward the surface. A circuit-enclosure, or housing, is used to contact the skin surface of the patient with light provided by the first circuit being characterized in a first wavelength range. The first circuit also senses a PPG signal of the patient in response to the light being sent toward the surface. The second circuit senses artifacts due to surface motion, where such artifacts are attributable to contact-based surface motion at a portion of the housing that is in contact with the skin surface of the patient. The frequency range of the artifacts overlaps with the frequency range of the PPG sensed by the first wavelength and/or as affecting the light in the first frequency range. Further, the second circuit responds to the sensed PPG signal by processing the sensed PPG signal relative to the sensed artifacts to produce a version of the sensed PPG signal that is indicative of local blood volume and blood composition of the patient. The PPG signal indicative of local blood volume and blood composition of the patient is filtered by the second circuit to suppress noise therein due to the contact-based surface motion.

Other aspects of the disclosure are directed to related embodiments in which the contact is not necessarily effecting direct engagement between the housing and the skin. In one such embodiment, the second circuit includes an impedance-based sensor that measures the surface motion artifacts, and the second circuit senses artifacts attributable to indirect contact-based surface motion at a portion of the housing in response to the housing being in sufficient proximity of the skin surface to transfer energy between the skin surface and the impedance-based sensor.

The above summary is not intended to describe each embodiment or every implementation of the present disclosure. The figures, detailed description and claims that follow more particularly exemplify various embodiments.

BRIEF DESCRIPTION OF THE DRAWINGS

Aspects of the present disclosure may be more completely understood in consideration of the detailed description of various embodiments of the present disclosure that follows in connection with the accompanying drawings, in which.

Figure 1:
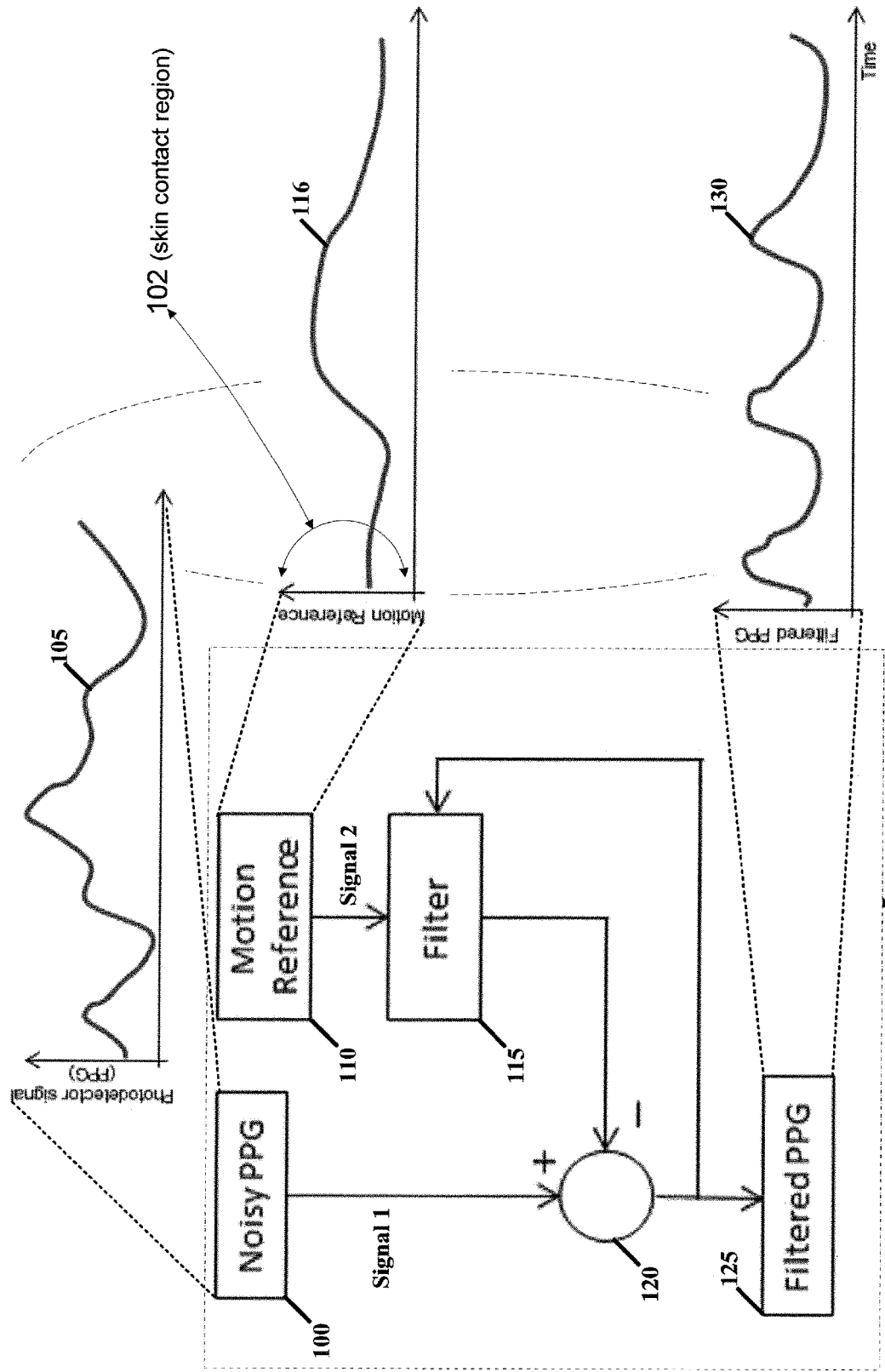
FIG. 1 shows an example block diagram of an apparatus for interfacing with a patient, consistent with various aspects of the present disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION

The present disclosure is believed to be useful for applications involving devices, apparatuses, and methods that determine local blood volume and blood composition in a subject and mitigate motion-induced errors that can occur during measurement. For instance, various aspects of the present disclosure are directed toward mitigation of artifacts in PPG signals due to the subtle movements of the devices/apparatuses (sensors), which are in same frequency range as the PPG signal itself, with respect to the tissue. Such sensors, consistent with various aspects of the present disclosure, can include structure that allows for placement of a patient's finger for determining local blood volume and blood composition. For instance, a patient will place his or her finger in, on, or near the sensor for PPG measurements. Based on the skin surface movements, motion defects occurs, and are determined/measured based on the surface movements. Accordingly, various aspects of the present disclosure include determination of at least one noise reference signal indicative of the artifacts that negatively affect the PPG signal(s) that is used to adaptively filter the PPG signal(s) to provide an accurate determination of PPG and/or a pulse oximetry measurement of a patient.

Various aspects of the present disclosure are directed toward apparatuses and methods for interfacing with a patient. The apparatus and methods are directed towards the apparatus operative for contacting the skin surface of the patient with one of the circuits illuminating tissue at the surface by sending light toward the surface. For example, the apparatus includes a housing for enclosing at least a first one of the circuits that contacts the skin surface of the patient, where the first circuit illuminates tissue at the surface by sending light toward the surface. Such contact at the skin surface is implemented in certain embodiments by a near contact and in other embodiments by an actual contact. The light provided by the first circuit is characterized as being in a first wavelength range. The first circuit also senses a PPG signal of the patient in response to the light being sent toward the surface.

The apparatus and methods for interfacing with a patient also include a second circuit that senses artifacts due to surface motion. In certain embodiments, the artifacts are characterized in that the artifact frequency range overlaps with the frequency range of the PPG sensed by the first wavelength and/or as affecting the light in the first frequency range. Further, the second circuit responds to the sensed PPG signal by processing the sensed PPG signal relative to the sensed artifacts to produce a version of the sensed PPG signal that is indicative of local blood volume and blood composition (e.g., heart rate or blood oxygen saturation) of the patient. The sensed PPG signal is filtered by the second circuit to suppress noise therein due to the surface motion.

In certain embodiments, the second circuit includes an impedance-based sensor that is used to measure the surface motion artifacts. In certain more specific embodiments, the impedance-based sensor determines electrical properties of the skin surface. Certain embodiments of the present disclosure are characterized in that the second circuit sends light toward the surface. The light sent by the second circuit is a second wavelength range that is different than the first wavelength range (sent by the first circuit). Additionally, in certain embodiments, the second circuit can include both an impedance-based sensor that measures surface motion artifacts of the patient that are both physiological and mechanical, and the second circuit that illuminates tissue at the surface at a second wavelength. In these such embodiments, the second circuit measures transmitted or reflected light being characterized by a second wavelength range and, in response thereto, measures physiological and mechanical surface motion artifacts of the patient and produce the filtered version of the sensed PPG signal.

Additionally, other embodiments, consistent with various aspects of the present disclosure are characterized in that the second circuit having an impedance-based sensor, which includes capacitance circuit and a computer that is electrically coupled to the capacitance circuitry. In such an embodiment, the impedance-based sensor measures physiological and mechanical surface motion artifacts of the patient. Further, the computer measures physiological and mechanical surface motion artifacts of the patient and produces the filtered version of the sensed PPG signal. In certain embodiments, the second circuit measures a transmitted or reflected PPG signal. Additionally, the second circuit can generate a noise-reference signal based on the sensed artifacts. The noise-reference signal is being characterized to correlate predominantly with the artifacts and minimally to the sensed PPG signal.

Various aspects of the present disclosure are also directed toward methods of interfacing with a patient. In such methods, the skin surface of the patient is contacted, and a light source is used to illuminate tissue at the surface, which sends light (in a first wavelength range) toward the surface. Additionally, a PPG signal of the patient is sensed in response to the light being sent toward the surface. Further, artifacts are sensed due to surface motion. The artifacts are characterized as also being in the first wavelength range, and in response to the sensed PPG signal, the sensed PPG signal is processed relative to the sensed artifacts to produce a version of the sensed PPG signal that is indicative of local blood volume and blood composition of the patient as filtered to suppress noise therein due to the surface motion.

Turning now to the Figures, FIG. 1 shows an example block diagram of an apparatus for interfacing with a patient, consistent with various aspects of the present disclosure. For instance, a noisy PPG block 100 represents a PPG signal having motion artifacts, relative to contact movement at a contact region 102 of the skin surface, that affect the signal, is measured in response thereto. The affected signals include the noisy PPG block 100, which illuminates tissue at the skin surface of a patient by sending light toward the surface. As discussed in further detail below the light is characterized as being in a first wavelength range. Such a measured noise PPG signal 100 is shown in the inset graph 105. In addition to the noisy PPG block 100, FIG. 1 shows a motion reference block 110. The motion reference block 110 denotes artifacts that occur due to surface motion between the contact region 102 of the skin surface and the housing 112 of the PPG apparatus. As shown in the inset, the artifacts are represented by a motion reference graph 116. Preferably, an outer surface of the housing 112 would contact the contact region 102 of the skin surface, directly or indirectly (e.g., through a light-passing intervening structure or medium for its impedance/capacitance aspects). As noted above, certain in embodiments, the artifacts can be characterized due to the artifact frequency range overlapping with the frequency range of the PPG (typically ranging from 0.1-30 Hz) as sensed by the first wavelength and as affecting the light in the first frequency range.

The motion reference block 110 passes the signal representing the artifacts (Signal 2) through a filter block 116. Additionally, a signal (Signal 1) representing the noisy PPG is passed from the noisy PPG block 100. Signals 1 and 2 are provided to a processor block 120. The processor block 120 responds to the PPG signal (Signal 1) by processing the sensed PPG signal relative to the sensed artifacts (Signal 2) to produce a filter version, represented by filtered PPG block 125, of the sensed PPG signal that is indicative of local blood volume and blood composition of the patient. The filtered version of the sensed PPG signal is shown in the inset graph 130. The filtered PPG block 125 suppresses the noise due to the surface motion.

Figure 2:
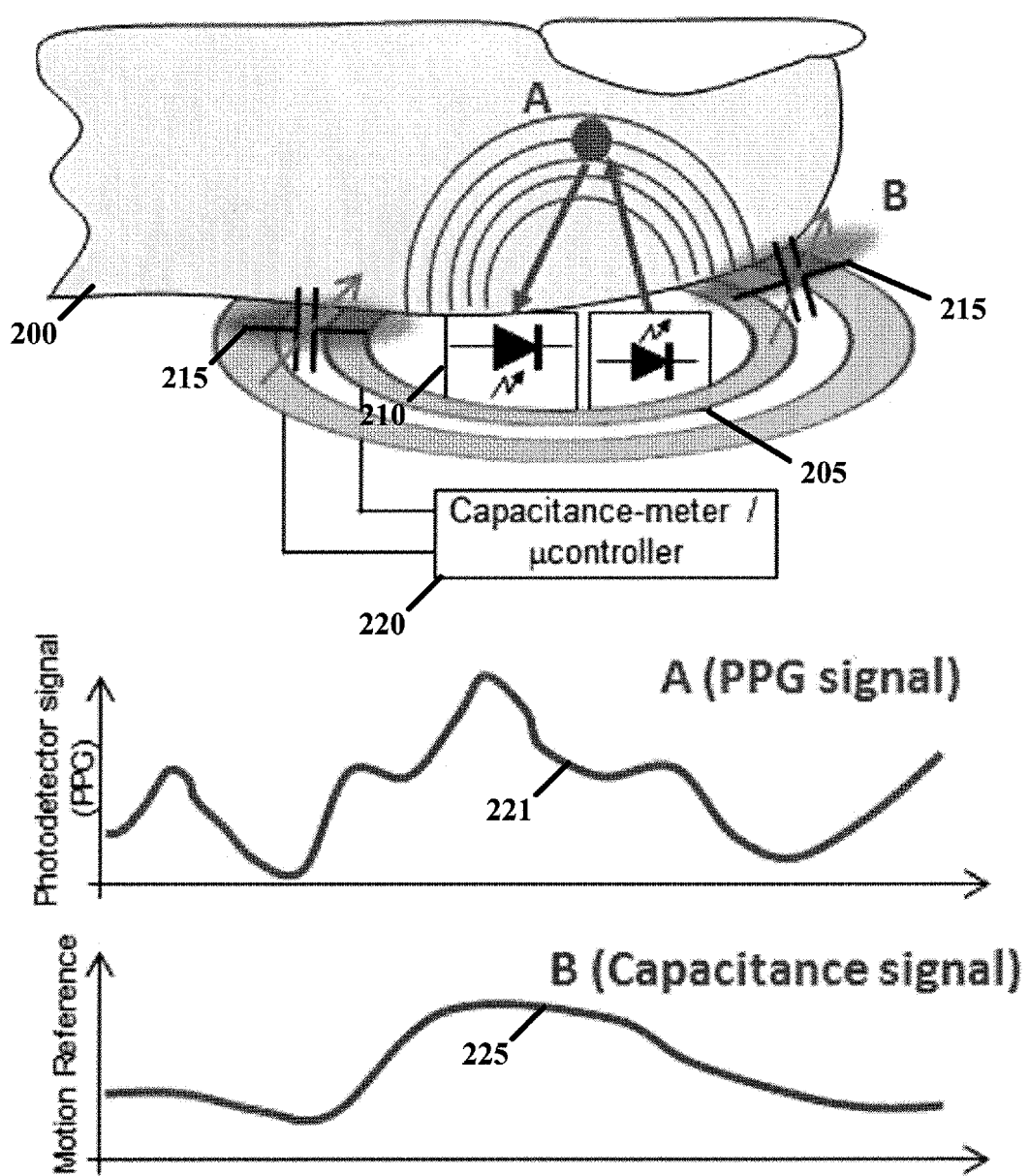
FIG. 2 shows an example PPG signal collector and determination of motion artifacts by capacitance circuitry, consistent with various aspects of the present disclosure.

FIG. 2 shows an example PPG signal collector and determination of motion artifacts by capacitance circuitry, consistent with various aspects of the present disclosure. Various aspects of the present disclosure are detected toward extraction of a noise-reference signal as can be used to filter out noise in a collected PPG signal, for example, as discussed with reference to FIG. 1. For instance, FIG. 2 shows a finger 200 of a patient making contact with a sensor or apparatus. A light source 205 shines light toward the skin-to-surface contact, which penetrates the finger 200 (shown as point A). The light reflects, and is measured by a photo collector 210 (e.g., a photodiode). This light path is the collected PPG signal. An optically measured PPG signal is determined by measuring the pulsatile change in local blood volume under the action of the pressure pulse generated by the heart's contraction. FIG. 2 also shows capacitance circuitry 215 that is used to determine the motion artifacts by measuring the subtle motion changes of the finger at the contact. The artifacts, in the form of capacitance measured by the capacitance circuitry 215, are provided to a capacitance-meter/microcontroller 220. FIG. 2 also shows an example PPG signal collected by the photo collector 210 in graph 221, and an example capacitance signal measured by the capacitance-meter/microcontroller 220 in graph 225.

Figure 3:
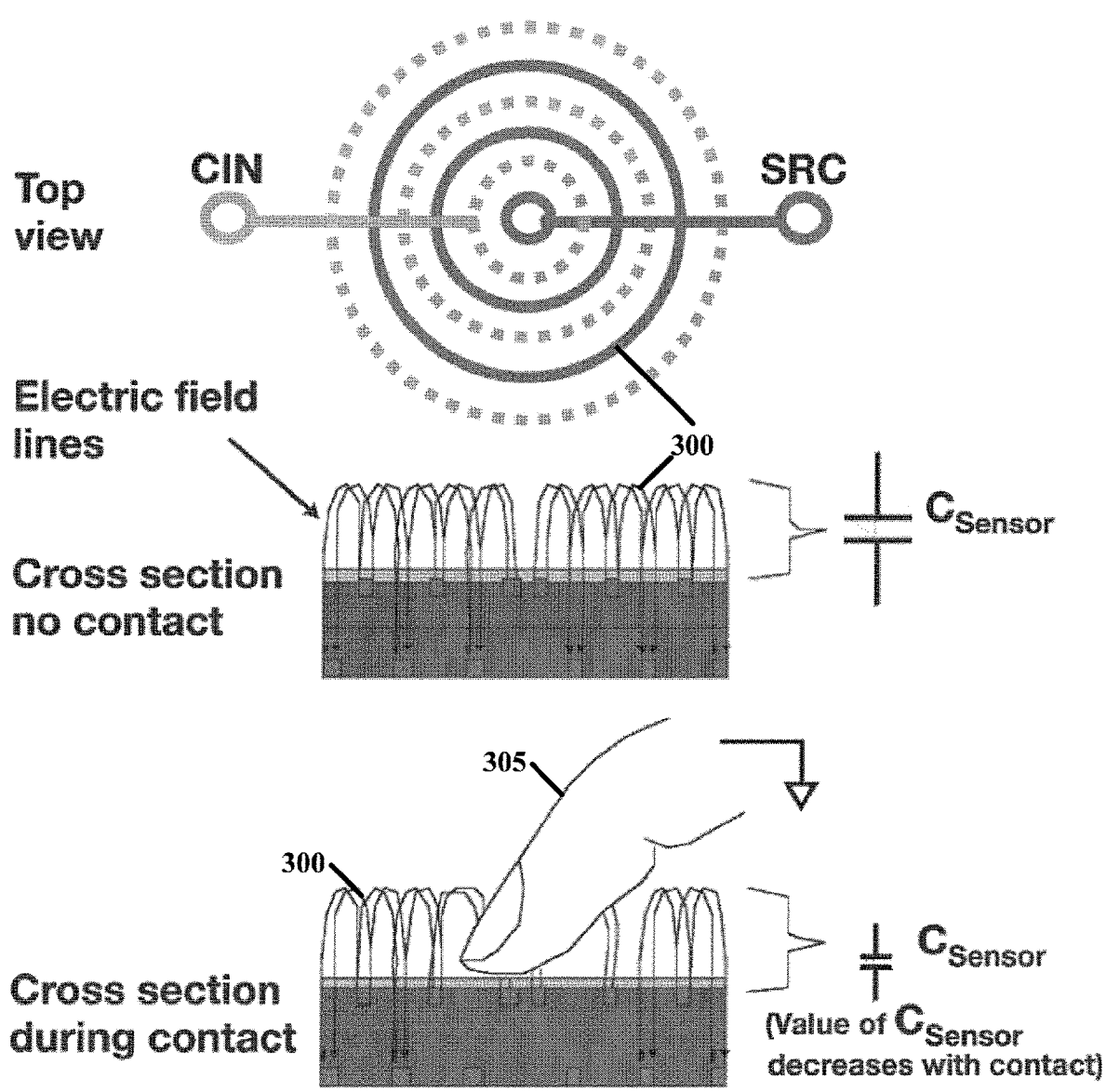
FIG. 3 shows an example capacitive sensing arrangement using conductive lines in a printed circuit board (PCB), consistent with various aspects of the present disclosure.

FIG. 3 shows an example capacitive sensing arrangement using conductive lines in a PCB, consistent with various aspects of the present disclosure. As shown in FIG. 3, a sensor, defined by one or more insulated conductive surfaces or lines 300, detects the capacitance change between these conductors when a finger 305 gets close and changes the dielectric properties of the capacitor. Changes of the interface between the sensors and the skin will also modulate the capacitance. The capacitance change can be measured using a simple microcontroller (see, e.g., Texas Instruments MSP430).

Figure 4:
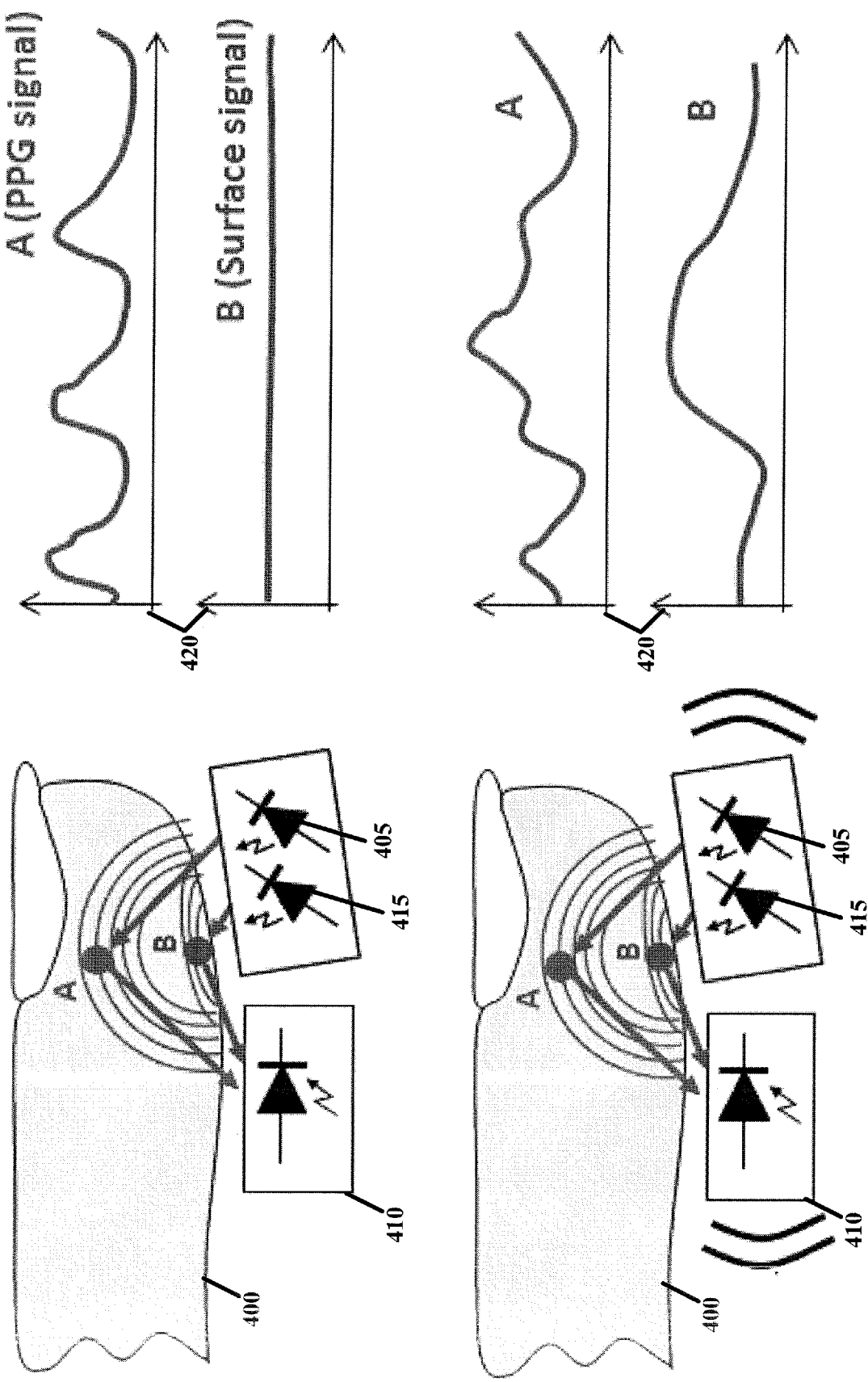
FIG. 4 shows a PPG signal collector and determination of motion artifacts by using an optical signal, consistent with various aspects of the present disclosure.

FIG. 4 shows a PPG signal collector and determination of motion artifacts by using an optical signal, consistent with various aspects of the present disclosure. The PPG signal is predominantly a measurement of a periodic change in local blood volume in a human/patient/person. As noted above, this signal can suffer from degradation due to motion artifacts. FIG. 4 shows a finger 400 of a patient making contact with a sensor or apparatus. A first light source 405 shines light toward the skin-to-surface contact, which penetrates the finger 400 (shown as path A). The light reflects, and is measured by a photo collector 410 (e.g., a photodiode). This light path is the collected PPG signal. An optically measured PPG signal is determined by measuring the pulsatile change in local blood volume under the action of the pressure pulse generated by the heart's contraction. A second light source 415 shines light toward the skin-to-surface contact, which penetrates the finger 400 (shown as path B). As noted above, an optically measured PPG signal is determined by measuring the pulsatile change in local blood volume under the action of the pressure pulse generated by the heart's contraction. More blood will absorb more light, and thus less light will pass through the tissue. If the detector is on the same side as the illuminator (reflectance PPG), then it is the amount of scattered light coming back to the detector which is modulated. PPG can be measured at many wavelengths, although some principles are usually guiding the selection. For the measurement of oxygen saturation (pulse oximetry), a combination of red and Infared (IR) lights are typically used because of the specific absorption spectra of hemoglobin and oxihemoglobin.

Red/IR light emitters also can have good transmission of these wavelengths through the tissue, which increases the signal in transmission mode and allows the interrogation of deep arteries. These wavelengths have low scattering coefficients. On the other hand, shorter wavelengths (yellow, green) have higher absorption coefficients as well as higher scattering coefficients. While detrimental for transmission mode (not enough light passes through the finger/ear lobe), this absorption generates more signal for reflectance mode. It also can sense more superficially. Successful reflectance mode PPG sensors have been constructed with green LEDs.

The skin of the finger 400, in response to light shown thereon by the second light source 415, has a distinct wavelength dependence for both absorption and scattering. The wavelength of the second light source 415 is absorbed only at the surface of the skin (where the remaining capillaries show much attenuated pulsation). Due to the wavelength of the second light source 415 being absorbed only at the surface of the skin, the reflectance of the light from the second light source 415 measured at the photo detector 410 is indicative of motion artifacts at the surface. For instance, the upper graphs 420 of FIG. 4 show an example where there is no movement of a sensor with respect to the skin surface. However, as shown in the lower graphs 425 of FIG. 4, if the sensor moves with respect to the skin surface, this surface signal (reference signal) modulates. Thus, because the surface signal (reference signal) modulates in response to movement, the signal is a reference signal to filter out motion-noise in a PPG signal. This signal can thus be used as a noise reference, as discussed with reference to FIG. 1.

Such an arrangement can utilize a photodetector, a light emitter (e.g., LED), and a second light emitter having an emission spectrum located close to the first light emitter (e.g., IR, red or green). In this manner due to the differing wavelength dependence for both absorption and scattering, a PPG signal is collected, and a separate optically-based signal is collected that captures the motion artifact due to sensor/tissue movements, but not the pulse signal. The wavelength of interest for such surface sensing would be in the blue/near-UV (as opposed to the red/IR wavelengths for a PPG signal), based on the strong adsorption of the melanin pigment present in the epidermis. Reducing the intensity of the emitted light will also contribute to a more superficial sensing, containing less of the pulsatile component.

Accordingly, because of the wavelength dependence of both absorption and scattering, a wavelength for a second light emitter can be selected which is absorbed only at the surface of the skin, where the remaining capillaries show much attenuated pulsation. The optically-based noise reference signal then becomes mainly a function of how the light is coupled into the skin, and where it is measured.

Further, as noted in FIG. 2 and FIG. 4, the artifacts of movement at the surface can be measured due to capacitance circuitry or a circuitry measuring the different wavelength of light absorbed only at the surface of a finger. Further, because the noise reference signals in those instances are collected based on separate circuitry, both the capacitance circuitry and the circuitry measuring the different wavelength of light absorbed only at the surface of a finger can be used to filter the PPG signal, as discussed with reference to FIG. 1.

As discussed herein, in measuring the PPG signal of a patient, the motion artifacts are determined when the patient's skin surface (e.g., digit/member) makes direct contact or medium-intervening contact in which the contact is indirect as indicated via with an impedance-based sensor. The impedance-based sensor can include or be implemented as part of a capacitive-touch apparatus such as a pulse oximeter or a smart tablet (e.g., smartphone) that also includes a camera and a light source. For instance, a patient can place his or her finger on the sensing-surface of the sensor (including circuitry as discussed herein) or a patient can place his or her finger for near contact (e.g., as would occur when energy is transferred between a capacitively-charged surface and a finger situated apart from one another by one to several millimeters). The capacitance circuitry, as described above, has sensitivity such that it can sense near contact of the patient. Further, in embodiments that use a second light source in mitigation of motion negatively affecting the PPG signal, light for both the PPG and the mitigation of motion can be provided from the sensor or smart tablet toward the skin surface. A camera (as is provided with the sensor or smart tablet) that is sensitive to both wavelengths can determine the motion artifacts based on wavelengths reflected/scattered at the skin surface (motion reference) versus wavelength absorbed more deeply and reflecting a stronger PPG signal, as presented for contact situations. The camera can measure the reflected/scattered light from the finger irrespective of the distance away from the finger (the angle of the light source(s) is not a significant factor).

Accordingly, in the above-discussed embodiments, the second circuit includes an impedance-based (e.g., capacitor-based) sensor that measures the surface motion artifacts attributable to contact-based surface motion at a portion of the housing when the housing is in sufficient proximity of the skin surface to transfer energy between the skin surface and the impedance-based sensor.

Figure 5A:
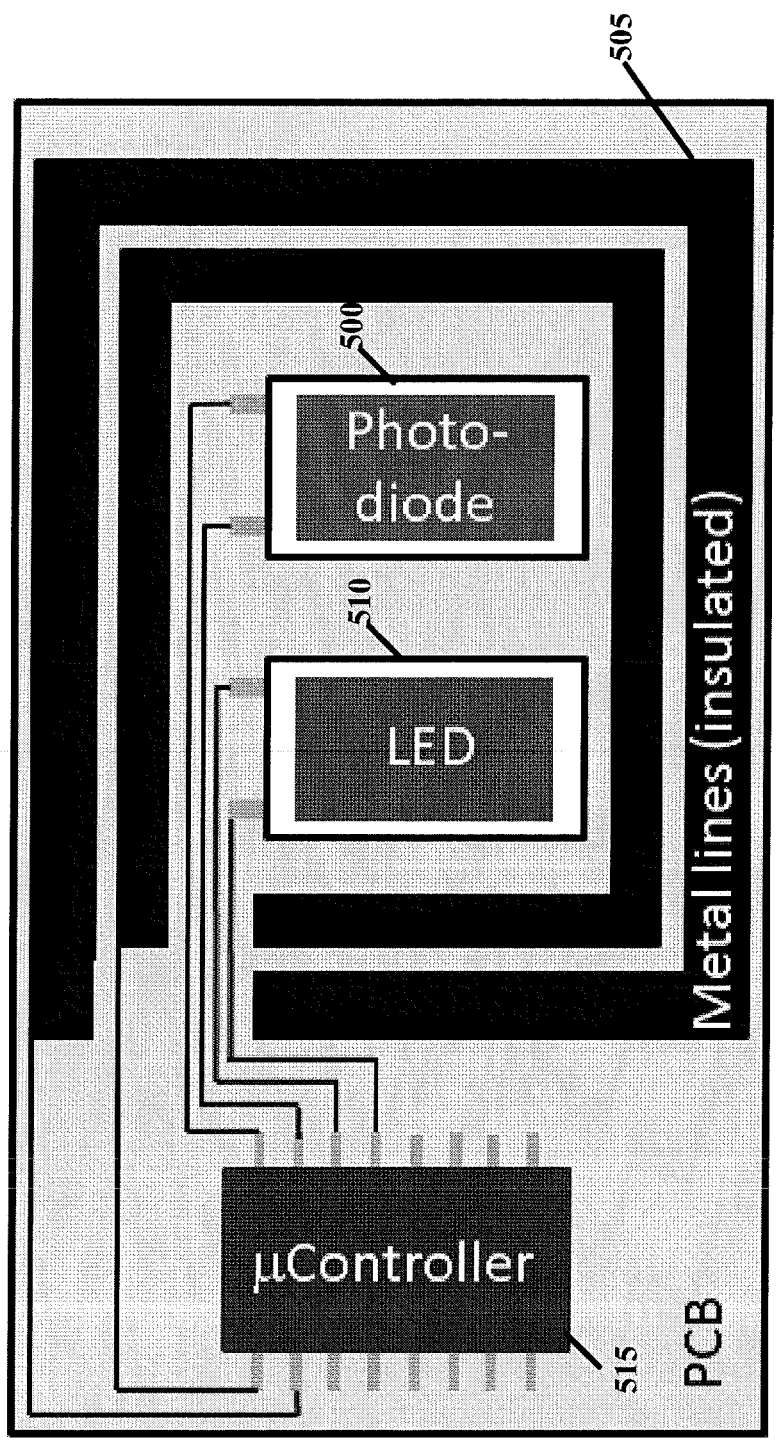
FIG. 5A shows an example arrangement of a sensor that includes a PPG signal detector and at least one noise reference signal circuit, consistent with various aspects of the present disclosure.
Figure 5B:
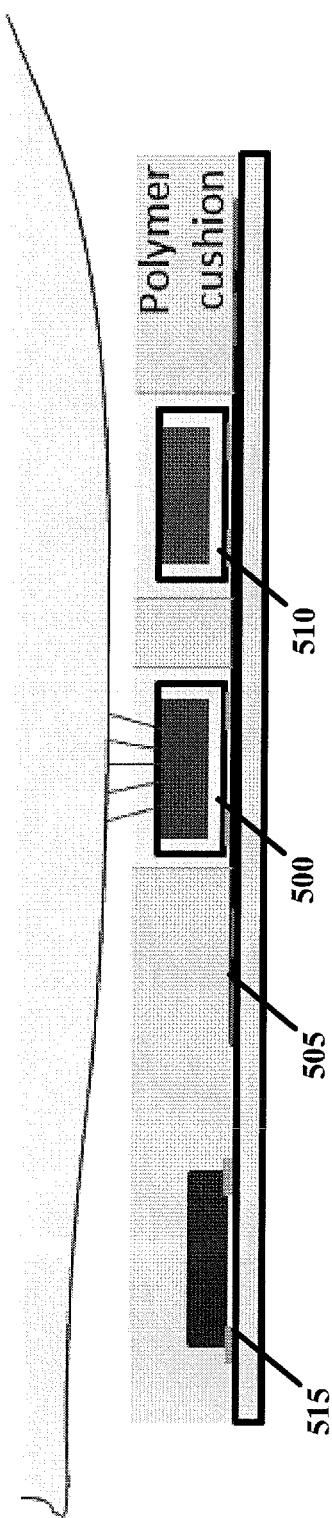
FIG. 5B shows another example arrangement of a sensor that includes a PPG signal detector and at least one noise reference signal circuit, consistent with various aspects of the present disclosure.
Figure 5C:
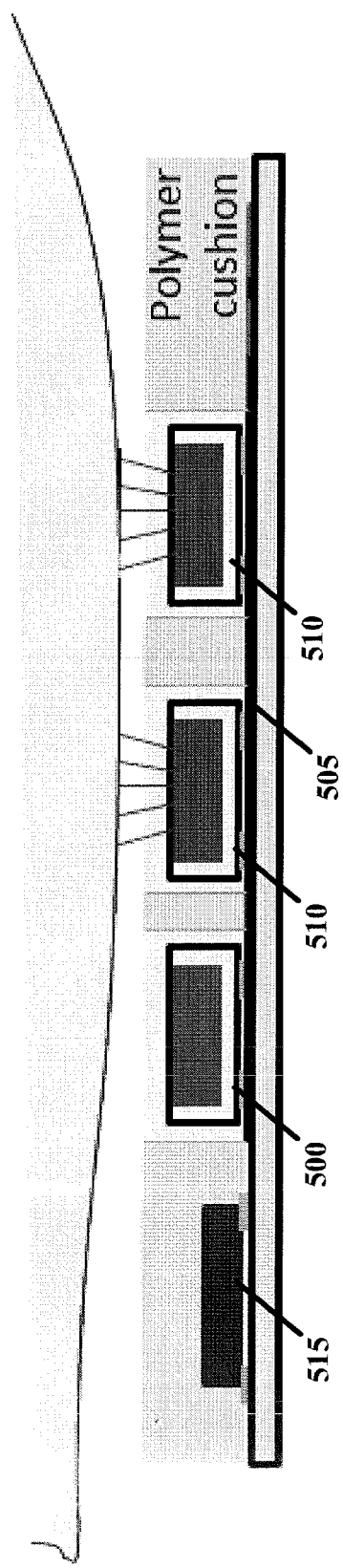
FIG. 5C shows another example arrangement of a sensor that includes a PPG signal detector and at least one noise reference signal circuit, consistent with various aspects of the present disclosure.
Figure 5D:
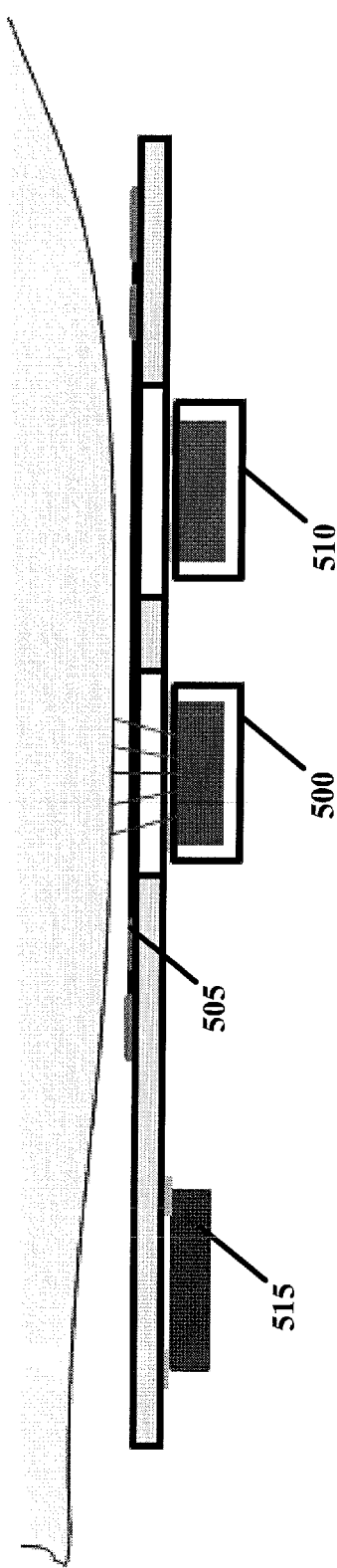
FIG. 5D shows another example arrangement of a sensor that includes a PPG signal detector and at least one noise reference signal circuit, consistent with various aspects of the present disclosure.

In each of FIGS. 5A-D, the arrangements shown include at least one emitter, a photodiode (for determining at least PPG signal), and a microcontroller. FIG. 5A shows an example arrangement of a sensor that includes a photodiode 500, capacitive circuitry 505 composed of two metal lines, encircles a light emitter 510 (which includes at least one light emitter), and a microcontroller 515. The sense lines can be on the same side as the other components as shown in FIG. 5B, or on opposite sides, as shown in FIG. 5D. As shown in FIG. 5C, the arrangement can include two emitters for arrangements using an optically-based noise reference signal. FIG. 5C also shows an optional capacitive sensor in instances when both the capacitance circuitry and the circuitry measuring the different wavelength of light absorbed only at the surface of a finger can be used to filter the PPG signal.

In certain instances, an optically-based noise reference signal can be sensed at both sides of tissue of a finger if transmission mode is performed. Further, an electrically-based noise reference signal can also utilize an impedance measurement, rather than a pure capacitance measurement. Such an impedance measurement can be performed by direct measurement of the impedance with metal contact surrounding the sensor. Because of the high impedance of the skin, such signals will also be very sensitive to skin/sensor contact, and therefore sensitive to relative motion. For all modes of electrical sensing, the sensor could be unique or composed of several sensitive surfaces.

For further discussion of physiologic monitoring, pulse oximetry or heart rate monitoring and mitigating motion artifacts of the measurement as relating to the embodiments and specific applications discussed herein, reference may be made to the underlying U.S. Provisional Patent Application, Ser. No. 61/693,270 filed on Aug. 25, 2012 (including the Appendix therein) to which priority is claimed. The aspects discussed therein may be implemented in connection with one or more of embodiments and implementations of the present disclosure (as well as with those shown in the figures). Moreover, for general information and for specifics regarding applications and implementations to which one or more embodiments of the present disclosure may be directed to and/or applicable, reference may be made to the references cited in the aforesaid patent application and published article, which are fully incorporated herein by reference generally and for the reasons noted above. In view of the description herein, those skilled in the art will recognize that many changes may be made thereto without departing from the spirit and scope of the present disclosure.

Various circuit-based building blocks and/or other modules may be implemented to carry out one or more of the operations and activities described herein and/or shown in the Figures. In such contexts, a "block" or "module" is a circuit that carries out one or more of these or related operations/activities. For example, in certain of the above-discussed embodiments, one or more blocks are discrete logic circuits or programmable logic circuits configured and arranged for implementing these operations/activities, as in the circuit modules shown in the Figures, such as the filter block or processor block shown in FIG. 1. In certain embodiments, the programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Based upon the above discussion and illustrations, those skilled in the art will readily recognize that various modifications and changes may be made without strictly following the exemplary embodiments and applications illustrated and described herein. Furthermore, various features of the different embodiments may be implemented in various combinations. Such modifications do not depart from the true spirit and scope of the present disclosure, including those set forth in the following claims.

What is claimed is:

1. An apparatus for interfacing with a subject, the apparatus comprising:
a housing including a light emitter, and a first circuit and a physiological sensor circuit, the first circuit being configured and arranged to
illuminate tissue at a skin surface of the subject by sending light toward the skin surface, the light being characterized by a first wavelength range, and
sense a pulse photoplethysmography (PPG) signal of the subject in response to the sent light being sent toward the skin surface while the housing is in contact and while the housing is near contact with the skin surface of the subject; and the physiological sensor circuit is configured and arranged with:
the light emitter being configured and arranged to sense artifacts attributable to surface motion of the skin surface with respect to the housing by sending additional light toward the tissue at the skin surface at a reduced intensity than the sent light and detecting modulation therefrom, wherein the detected modulation includes changes corresponding to the skin surface and is indicative of the additional light as reflected from the same tissue of the skin surface as the PPG signal is sensed from; and
wherein the physiological sensor circuit is configured and arranged with a signal-processing filter to respond to the sensed PPG signal by using the detected modulation from the additional light sent at the reduced intensity to produce a version of the sensed PPG signal that is indicative of local blood volume and blood composition of the subject and that is filtered to suppress noise therein due to the surface motion, wherein a frequency range of the sensed artifacts overlap with a frequency range of the sensed PPG signal wherein the physiological sensor circuit further includes an impedance-based sensor having conductors to transfer energy there between, and configured and arranged to measure changes in properties of the transferred energy which is further between the physiological sensor circuit and pulsatile tissue of the subject, and therefrom, sense artifacts attributable to the surface motion as an interface between the skin surface of the subject and the housing changes by creating an electrical field over the housing and detecting an impedance change between the conductors of the physiological sensor circuit, wherein the impedance-based sensor is configured and arranged to determine electrical properties via the skin surface of the subject and wherein the conductors of the impedance-based sensor include at least one conductive line encircling the first circuit such that the conductors surround the first circuit and the light emitter, and wherein the physiological sensor circuit is configured and arranged with the signal-processing filter to respond to the sensed PPG signal by using the detected modulation and the impedance change between the conductors of the physiological sensor circuit to produce a filtered version of the sensed PPG signal.

2. The apparatus of claim 1, wherein the physiological sensor circuit includes: the impedance-based sensor, including capacitance circuitry, configured and arranged to measure physiological and mechanical surface motion artifacts of the subject; and a computer that is electrically coupled to the capacitance circuitry and configured and arranged to measure physiological and mechanical surface motion artifacts of the subject and produce a filtered version of the sensed PPG signal.

3. The apparatus of claim 1, wherein the physiological sensor circuit includes the impedance-based sensor configured and arranged to measure surface motion artifacts of the subject that are both physiological and mechanical.

4. The apparatus of claim 1, wherein the physiological sensor circuit includes the impedance-based sensor, including the conductors, configured and arranged to measure the artifacts, and wherein the physiological sensor circuit is further configured and arranged to sense artifacts attributable to non-contact-based and contact-based surface motion at a portion of the housing in response to a distance between the housing and the skin surface, and the distance changing as the skin surface approaches, but before contacting, the housing, such that the housing is in sufficient proximity of the skin surface to transfer energy between the skin surface and the impedance-based sensor and, in response, the impedance-based sensor is configured and arranged to detect the impedance change, via a capacitance measurement, between the conductors of the impedance-based sensor.

5. The apparatus of claim 1, wherein the physiological sensor circuit is further configured and arranged to detect the impedance change between the conductors of the physiological sensor circuit by measuring capacitance changes between the conductors, the conductors including at least two metal lines that surround the first circuit that includes a photodiode and a light emitter circuit.

6. The apparatus of claim 1, wherein the first circuit includes a photodiode and a light emitter circuit, and the conductors of the physiological sensor circuit include at least two metal lines that encircle the photodiode and the light emitter circuit.

7. The apparatus of claim 6, wherein the housing is configured and arranged to allow for placement of a digit of the subject therein, and the sensed artifacts are indicative of relative movement of the first circuit with respect to the skin surface of the digit.

8. An apparatus for interfacing with a subject, the apparatus comprising:
a housing including:
first means for
illuminating tissue at a skin surface of the subject by sending light toward the skin surface, the light being characterized by a first wavelength range, and
sensing a pulse photoplethysmography (PPG) signal of the subject in response to the light being sent toward the skin surface; and
physiological sensor means, including impedance circuitry having conductors, for transferring energy between the conductors, measuring changes in properties of the transferred energy which is indirectly between the physiological sensor means and pulsatile tissue of the subject, and therefrom sensing artifacts due to surface motion as an interface between the skin surface of the subject and the housing changes, by;
creating an electrical field over the housing, and
detecting an impedance change between the conductors of the impedance circuitry, wherein the conductors of the impedance circuitry include at least one conductive line encircling the first means such that the at least one conductive line surrounds the first means,
wherein the physiological sensor means further includes a signal-processing filter for responding to the sensed PPG signal by using the detected impedance change to process the sensed PPG signal relative to the sensed artifacts, and therefrom producing a version of the sensed PPG signal that is indicative of local blood volume and blood composition of the subject as filtered to suppress noise therein due to the motion at the skin surface, wherein the sensed artifacts are indicative of relative movement of the first means with respect to the skin surface of the subject, and wherein the sensed artifacts are sensed at the same tissue of the skin surface as the PPG signal is sensed from.

9. A method of interfacing with a subject, the method comprising:
using a light source of an apparatus, the apparatus having a housing for the light source and a physiological sensor circuit including an impedance-based sensor having conductors, to illuminate tissue at a skin surface of the subject, thereby sending light thereat, the light being characterized by a first wavelength range;
sensing a pulse photoplethysmography (PPG) signal of the subject in response to the light being sent toward tissue of the skin surface using a detector circuit of the physiological sensor circuit while the housing is in contact and while the housing is near contact with the skin surface of the subject; and
transferring energy between the conductors of the impedance-based sensor and measuring changes in properties of the transferred energy which is between the impedance-based sensor and pulsatile tissue of the subject, and therefrom, sensing artifacts due to surface motion and a change in an interface between the skin surface approaches the housing by:

sending light characterized by, and detecting modulation therefrom, a second wavelength range toward the same skin surface, wherein the modulation of the second wavelength range includes changes corresponding to the skin surface and is indicative of reflected light at the same tissue of the skin surface as the PPG signal is sensed from, the light characterized by the second wavelength range being at a lower intensity than the light characterized by the first wavelength range, and creating an electrical field over the housing; and detecting an impedance change between the conductors of the impedance-based sensor, wherein the conductors include at least one conductive line encircling the light source and the detector circuit such that the at least one conductive line surrounds the light source and the detector circuit, and wherein, in response to the sensed PPG signal, using the modulation of the second wavelength range and the detected impedance change in the dielectric properties between the conductors, via the physiological sensor circuit and a signal-processing filter, to produce a version of the sensed PPG signal that is indicative of local blood volume and blood composition of the subject as filtered to suppress noise therein due to the surface motion.

10. The method of claim 9, wherein sensing the artifacts includes:

sending the light toward the skin surface, the light being characterized by the second wavelength range that is different than the first wavelength range and including the lower intensity of light than the light characterized by the first wavelength range; and sensing the artifacts based on wavelengths in the second wavelength range that are reflected or scattered by the skin surface, the artifacts being indicative of movement of the same skin surface and as sensed based on the wavelengths in the second wavelength range and at the lower intensity which contains less of a pulsatile component than wavelengths in the first wavelength.

11. The method of claim 9, wherein sensing the artifacts includes:

sending the light characterized by both the first and second wavelength ranges toward the skin surface, the light being characterized by the second wavelength range that is absorbed at the surface of the skin and is within a near-ultraviolet or blue wavelength range, and sensing, by a camera, the PPG signal of the subject in response to the light based on wavelengths in the first wavelength range and sensing the artifacts based on wavelengths in the second wavelength range by generating a spectral image of the skin surface from light reflected or scattered by the skin surface in both the first and second wavelength ranges, wherein the camera is decoupled from movement of the skin surface.

12. The method of claim 9, wherein sensing the artifacts further includes:

creating the electrical field over the housing and detecting the impedance change across the conductors of the physiological sensor circuit, in response to changes in a volume or a surface area of the pulsatile tissue of the subject caused by the change in the interface between the skin surface and the housing.

13. The method of claim 9, wherein sensing the artifacts includes:

sending the light characterized by the second wavelength range toward the skin surface and, therefrom, measuring wavelengths reflected or scattered by the skin surface, and sensing the artifacts based on wavelengths in the second wavelength range that are reflected or scattered by the skin surface and responsive to changes in a volume or a surface area of the pulsatile tissue of the subject caused by the skin surface approaching or moving away from the housing, thereby causing the change in the interface between the skin surface and the housing.

* * * * *